United States Patent [19]
Clinton et al.

[11] Patent Number: 5,545,145
[45] Date of Patent: Aug. 13, 1996

[54] PEN NEEDLE DESPENSER

[75] Inventors: Mary B. Clinton, Suffern, N.Y.; John B. Wilson, Wanaque, N.J.

[73] Assignee: Becton Dickinson and Company, Franklin Lakes, N.J.

[21] Appl. No.: 291,269

[22] Filed: Aug. 16, 1994

[51] Int. Cl.$^6$ .................................................... A61M 5/32
[52] U.S. Cl. ........................... 604/192; 604/110; 604/263; 206/366
[58] Field of Search ..................................... 604/110, 192, 604/198, 263; 206/363–366; 221/66

[56] References Cited

U.S. PATENT DOCUMENTS

| | | | |
|---|---|---|---|
| 1,050,043 | 1/1913 | Sellar | 206/366 |
| 1,501,324 | 7/1924 | Eisele | 206/366 |
| 1,599,881 | 9/1926 | Eisele | 206/366 |
| 2,726,759 | 12/1955 | Fleming | 206/366 |
| 4,643,199 | 2/1987 | Jennings, Jr. et al. | 604/110 |
| 4,781,697 | 11/1988 | Slaughter | 604/263 |
| 4,848,569 | 7/1989 | Leishman | 206/365 |
| 4,968,304 | 11/1990 | Alter et al. | 604/192 |
| 5,057,088 | 10/1991 | Narayanan et al. | 604/198 |
| 5,403,288 | 4/1995 | Stanners | 604/232 |

FOREIGN PATENT DOCUMENTS 308714  10/1955  Switzerland ........................ 206/366

*Primary Examiner*—John D. Yasko
*Attorney, Agent, or Firm*—Alan W. Fiedler

[57] ABSTRACT

An apparatus is provided for safely and conveniently holding and dispensing needle assemblies. The apparatus includes a generally tubular holder with opposed dispensing and inserting ends and an elongate passageway extending therebetween. The tubular holder is dimensioned to slidably receive needle assemblies therein in axial alignment with one another. Separator disks are disposed between adjacent needle assemblies in the holder, and an end disk is disposed between the inserting end of the holder and the needle assembly adjacent thereto. The separator disks and the end disk are color coded to be readily visible through a window in the holder. The needle assembly nearest the dispensing end can be mounted to medication delivery pen or other hypodermic syringe and may be removed from the holder. The used needle assembly may then be inserted into the inserting end of the holder. This process is repeated for each administration of medication until the supply of needles is exhausted. The number of needle assemblies remaining can be readily observed through the window by tracking the incremental advancement of color coded separator disks.

20 Claims, 4 Drawing Sheets

5,545,145

PEN NEEDLE DESPENSER

BACKGROUND OF THE INVENTION

1. Field of the Invention

The present invention relates to a holder for hypodermic needles, and more particularly to an apparatus that holds and dispenses sterile needles for medication delivery pens and safely stores the needles after use.

2. Description of the Prior Art

Many patients, such as diabetics, must inject themselves with precisely measured doses of medication several times each day. This regimen has been facilitated in recent years by a convenient type of hypodermic syringe that is referred to as a medication delivery pen. A prior art medication delivery pen is identified generally by the numeral 10 in FIG. 1. Pen 10 contains a cartridge with sufficient medication for several doses. The prior art cartridge has opposed proximal and distal ends. The distal end is closed by a pierceable and resealable rubber septum identified by the numeral 12 in FIG. 1. The proximal end receives a stopper in sliding fluid-tight engagement. The prior art cartridge is disposed in an elongate pen-like body 14 with a proximal end (not shown) and an opposed distal end 16. The proximal end of the pen body includes a plunger for selectively driving the stopper of the cartridge in the distal direction and a dose setting mechanism for determining the distance through which the plunger and stopper can move. Distal end 16 of pen body 14 includes an array of threads 18 for threaded engagement with a pen needle assembly 20. Prior art pen needle assembly 20 includes a needle cannula 21 with opposed proximal and distal tips 24 and 22 and a mounting cap 26 which surrounds the proximal tip 24. Mounting cap 26 is threadedly engageable with distal end 16 of pen body 14. A safety shield 28 is releasably engaged over distal point 22 and portions of cap 26 to prevent accidental needle sticks.

A person who must periodically inject doses of medication will carry a medication delivery pen 10 and a supply of pen needle assemblies 20. Each pen needle assembly 20 has its needle cannula 21 safely and sterilely sealed in its own shield 28, and is accessed immediately prior to administering a dose of medication. Prior art pen needle assembly 20 then is mounted to distal end 16 of prior art pen 10. This mounting causes proximal point 24 of needle cannula 21 to pierce rubber septum 12 of the cartridge, to place needle cannula 21 in communication with the medication. Pen 10 then is used to inject the selected dose of the medication. After completing the injection, needle assembly 20 is separated from pen 10 and is discarded. Pen 10 may be used repeatedly in this manner until the medication is exhausted.

Prior art pens offer many conveniences and efficiencies. However, the storage of needles and the disposal of used needles has presented problems. In particular, supplies of new needles often are loosely scattered in the bottom of purses or briefcases, and used needles are often disposed of unsafely.

SUMMARY OF THE INVENTION

The present invention is directed to a storing and dispensing apparatus for needle assemblies used with hypodermic syringes, and preferably pen needles used with medication delivery pens. The apparatus includes an elongate tubular holder having opposed first and second ends and a passageway extending therebetween. The passageway is dimensioned and configured to store a plurality of needle assemblies, including their respective shields and mounting caps, in axial end-to-end relationship. The holder may include an elongate window to permit observation of needle assemblies stored in the passageway. The holder may further include a lid hingedly connected to the first end and a finger protection ring mounted to the second end. The finger protection ring may be configured to permit insertion of a used needle while substantially preventing insertion of a finger.

The apparatus of the subject invention may further include a plurality of visually observable separators slidably received in the holder between sterile needle assemblies. The disks also may be dimensioned to be frictionally retained in the lid hinged to the first end of the holder.

The apparatus also may include a clip securely connected to the tubular holder, and releasably connected to a medication delivery pen.

A plurality of sterile needle assemblies may be placed in the holder by the needle manufacturer, such that the proximal end of each sterile needle cannula points toward the first end of the tubular holder. The sterile needle assemblies may be separated by the separators. An end marker that is visually distinct from the separators may be disposed between the second end of the holder and the sterile needle assembly closest thereto. At least some of the separators may be viewable through the elongate window in the holder. The needle located at the first end of the holder has its threadedly engageable mounting cap disposed outwardly to accommodate the cooperating threaded distal end on a pen or other syringe. Thus, the first end of the holder and the distal end of a pen or other syringe may be mated and turned with respect to each other, such that the needle assembly becomes attached to the pen and may be readily withdrawn from the holder. The safety shield may be removed from the distal end of the needle, and the pen then is ready for administering an injection.

Following use, the safety shield may be replaced over the needle cannula and the shielded needle assembly may be returned to the holder through the second end. Specifically, the used needle assembly on the pen is inserted, distal end first, in the second end of the holder and through the finger protection ring. The pen is unscrewed from the needle assembly and then removed from the holder. The finger protection ring keeps the needle assembly in the holder. During insertion, the used needle urges the other used and sterile needle assemblies, the separators and the end marker toward the first end, to position the next sterile needle assembly, for removal. The advancement of the separators and the end marker through the holder, as successive needles are used and reinserted, can be viewed through the elongate window to determine the number of sterile needle assemblies still available. When no end marker or separators appear in the window, all of the needle assemblies in the holder have been used. Used needle assemblies are oriented oppositely in the holder, and hence can not be attached to a pen inadvertently.

DETAILED DESCRIPTION OF THE PREFERRED EMBODIMENT

Figure 1:
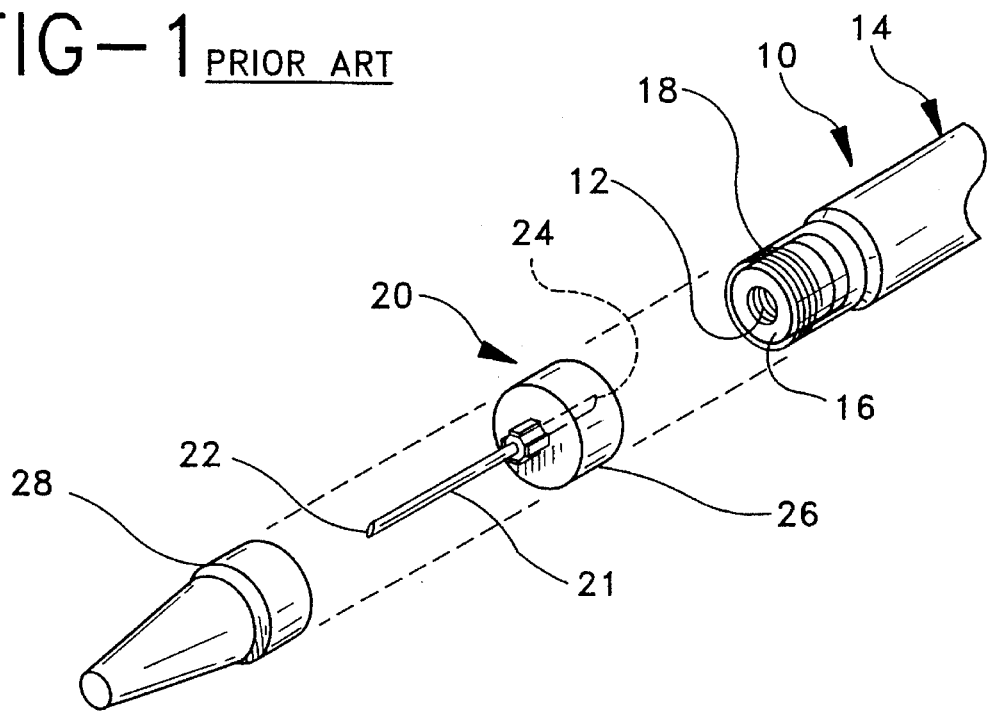
FIG. 1 is an exploded perspective view of a prior art needle and the distal end of a prior art medication delivery pen with which the present invention is intended to be used.

A storage and dispensing apparatus in accordance with the subject invention is identified generally by the numeral 30 in FIGS. 2–8. Apparatus 30 includes a generally tubular holder 32 with opposed dispensing and inserting ends 34 and 36 and a passageway 38 extending therebetween. Passageway 38 defines a substantially uniform inside diameter "a" which is approximately equal to or slightly greater than the maximum outside diameter of needle assembly 20 as depicted in FIG. 1. Thus, a shielded needle assembly 20 can be slidably received within tubular holder 32. Holder 38 further defines an outside diameter "b" which is approximately equal to the outside diameter of pen 10 with which apparatus 30 may be used.

Apparatus 30 further includes a lid 42 hingedly mounted to dispensing end 34 of holder 32. Lid 42 is a short cylindrical member having a hollow inside cavity 44 with a diameter "a" substantially equal to the diameter defined by passageway 38 of holder 32. The articulation of lid 42 to holder 32 is achieved by hinge 46. Hinge 46 may be unitarily molded with both holder 32 and lid 42. However, hinge 46 may be separate from either lid 42 or holder 32 and may be snapped into engagement therewith.

A finger protection ring 48 is fixedly secured to insertion end 36 of holder 32. Finger protection ring 48 includes an array of generally radially aligned inwardly projecting flexible fingers 50. Flexible fingers 50 of finger protection ring 48 are sufficiently close and offer sufficient resistance to make insertion of a finger into holder 32 difficult. However, flexible fingers 50 will yield in response to forces generated by a prior art needle assembly 20 as explained further below. Fingers 50 also prevent reattachment of a used needle assembly 20 to pen 10.

Apparatus 30 further includes a plurality of separator disks 52 which define diameters approximately equal to inside diameter "a" of passageway 38 in holder 32. Thus, separator disks 52 can be inserted into holder 32 and may be slid axially therealong. Additionally, separator disks 52 can be slidably inserted into and retained in lid 42. Separator disks 52 are color coded, and preferably are of identical colors (e.g., green). Additionally, separator disks 52 are sufficiently thick to be substantially rigid and to be readily visible through window 40 of holder 32.

Apparatus 30 further includes an end disk 54 that may be substantially identical to separator disks 52 in all respects except color. Thus, for separator disks 52 that are colored green, end disk 54 may be colored red.

Figure 7:
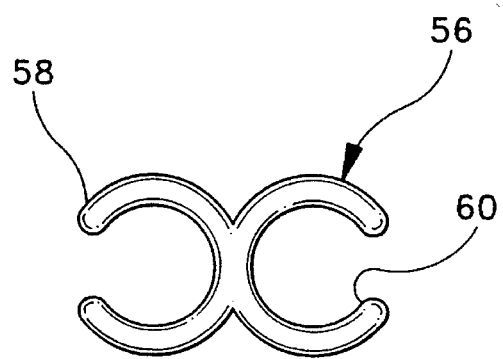
FIG. 7 is a top plan view of a mating clip for attaching a needle holder of the invention to a medication delivery pen dispenser.
Figure 8:
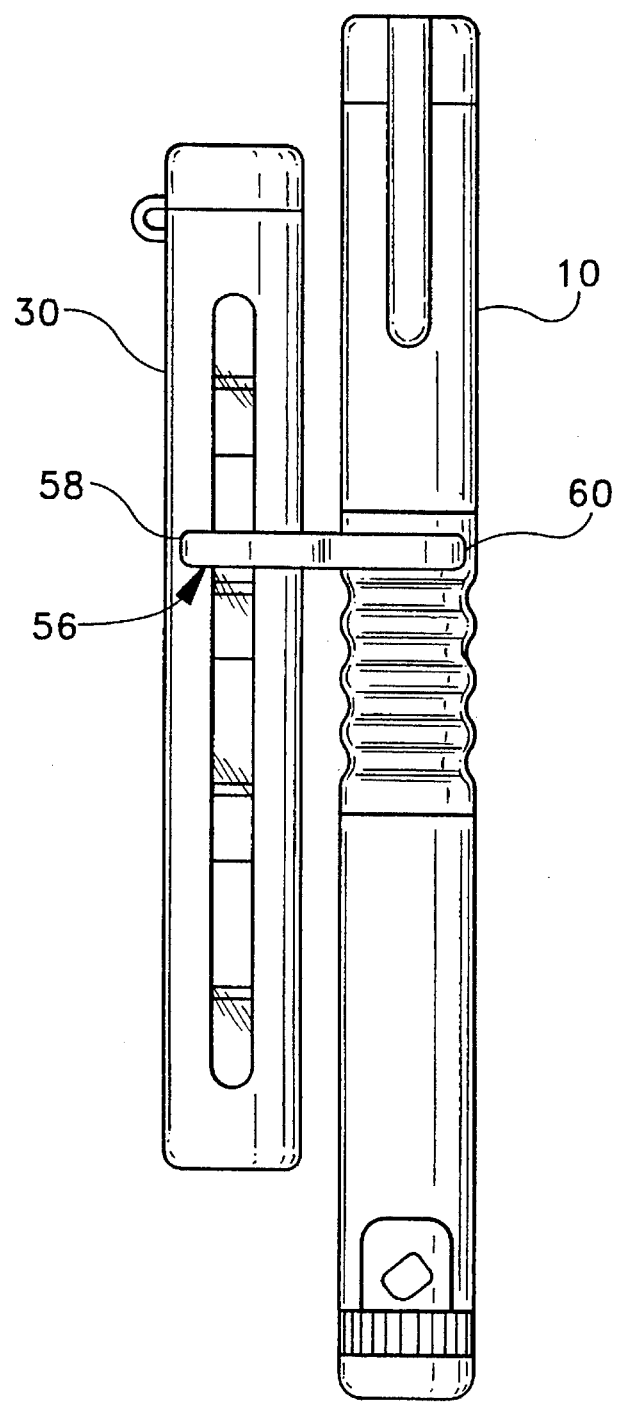
FIG. 8 is a front elevational view of a pen and a holder attached to a mating clip.

With reference to FIGS. 7 and 8, apparatus 30 further includes a mating clip 56 that is unitarily molded from a resilient plastic material and defining oppositely directed C-shaped clip portions 58 and 60 respectively. As explained further herein, each C-shaped portion 58, 60 of clip 56 is dimensioned to resiliently engage either a holder 32 or a pen body 14.

Apparatus 30 is used by initially inserting end disk 54 into dispensing end 34 of holder 32. A needle assembly 20 then is inserted into dispensing end 34 of holder 32, such that safety shield 28 and distal tip 22 of needle cannula 21 point toward inserting end 36 of holder 32. It follows that proximal point 24 of needle cannula 21 will point toward dispensing end 34 of holder 32. The insertion of needle assembly 20 into dispensing end 34 of holder 32 will urge end disk 54 closer to insertion end 36 of holder 32. A separator disk 52 then is inserted into dispensing end 34 of holder 32. Loading of apparatus 30 continues by alternately inserting needle assemblies 20 and separator disks 52 into dispensing end 34 of holder 32. Loading is completed by inserting the last needle assembly 20 into dispensing end 34 without inserting a corresponding separator disk. Thus, holder 32 will include an equal number of disks and needle assemblies. The disks will comprise one end disk 54 and a number of separator disks equal to the number "n" of needle assemblies 20 minus one (i.e., n−1). In the typical embodiment, holder 32 will contain a total of five needle assemblies 20. However, larger or smaller holders can be provided.

Apparatus 30 is used by initially opening lid 42 such that mounting cap 26 of sterile needle assembly 20 and proximal point 24 of the corresponding needle cannula are pointing outwardly from dispensing end 34. A foil or paper safety seal may extend across the proximal end of safety shield 28 to protectively enclose mounting cap 26 and needle cannula 21. The user of apparatus 30 will initially remove any protective seal that is provided on the needle assembly 20 to expose mounting cap 26 and proximal point 24. Distal end 16 of prior art pen 10 then is urged into dispensing end 34 such that proximal tip 24 of needle cannula 21 pierces rubber septum 12 of the cartridge in pen 10. After sufficient axial movement of pen 10 and apparatus 30 toward one another, pen 10 is rotated to threadedly engage mounting cap 28 of needle assembly 20. Pen 10 and holder 32 then are separated to withdraw sterile needle assembly 20 from holder 32.

Pen 10 will then be used in the conventional manner by setting a dose, removing safety shield 28 and injecting the selected dose of medication. Safety shield 28 then is replaced over distal tip 22 of needle cannula 21. The user will then hold pen 10 in one hand and holder 32 in the opposed hand and urge needle assembly 20 on distal end 16 of pen 10 into receiving end 36 of holder 32. This insertion will require flexible fingers 50 of finger protection ring 48 to yield. Additionally, insertion of needle assembly 20 into holder 32 will push end disk 54 and the adjacent axially aligned array of needle assemblies 20 and separator disks 52 toward dispensing end 34. After needle assembly 20 is substantially entirely within holder 32, pen 10 may be rotated relative to holder 32 to threadedly disengage pen 10 from needle assembly 20. Upon separation of pen 10 from needle assembly 20, fingers 50 of finger protection ring 48 may resiliently return toward an undeflected condition to prevent accidental sticks with proximal end 24 of a used needle cannula 21 adjacent insertion end 36 of holder 32. One separator disk 52 will then be in a position to be slidably removed from dispensing end 34 of holder 32 and may be stored in cylindrical opening 44 of cap 42. This will leave the next needle assembly in a position to be mounted to pen 10 immediately prior to the next required administration of a dose of medication.

Figure 2:
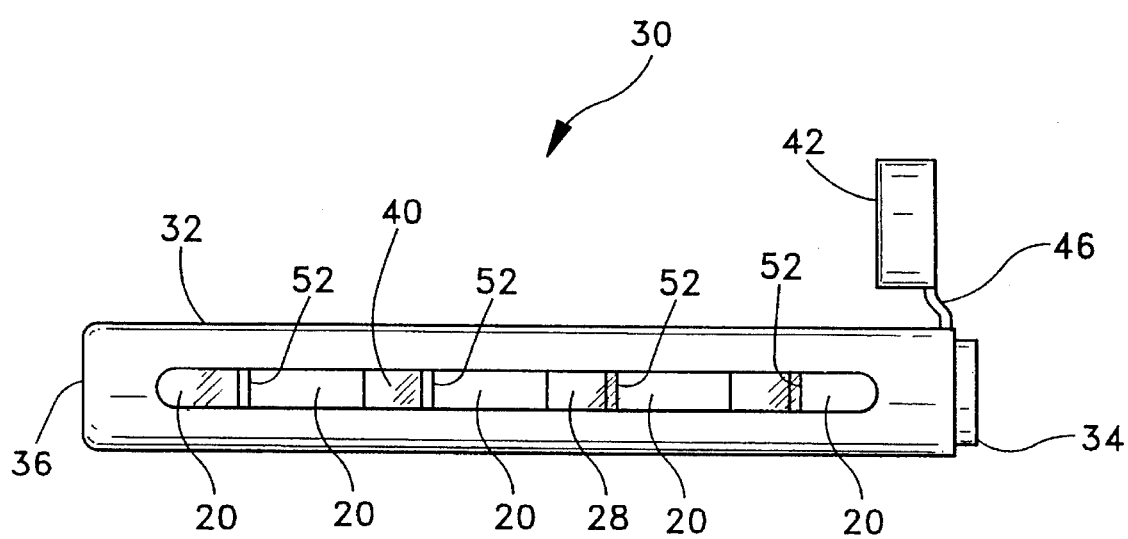
FIG. 2 is a side elevational view of a needle dispensing apparatus in accordance with the present invention.
Figure 3:
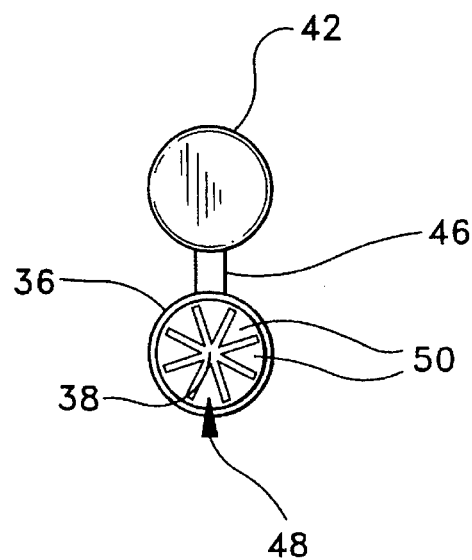
FIG. 3 is an end elevational view of the needle dispensing apparatus as viewed from the left side of FIG. 2.
Figure 4:
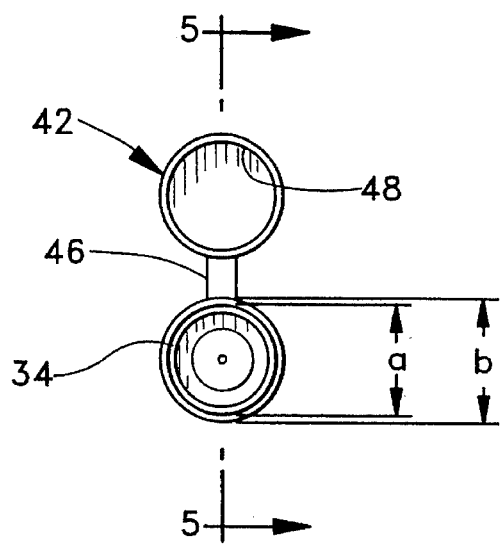
FIG. 4 is an end elevational view as viewed from the right side of FIG. 2.
Figure 5:
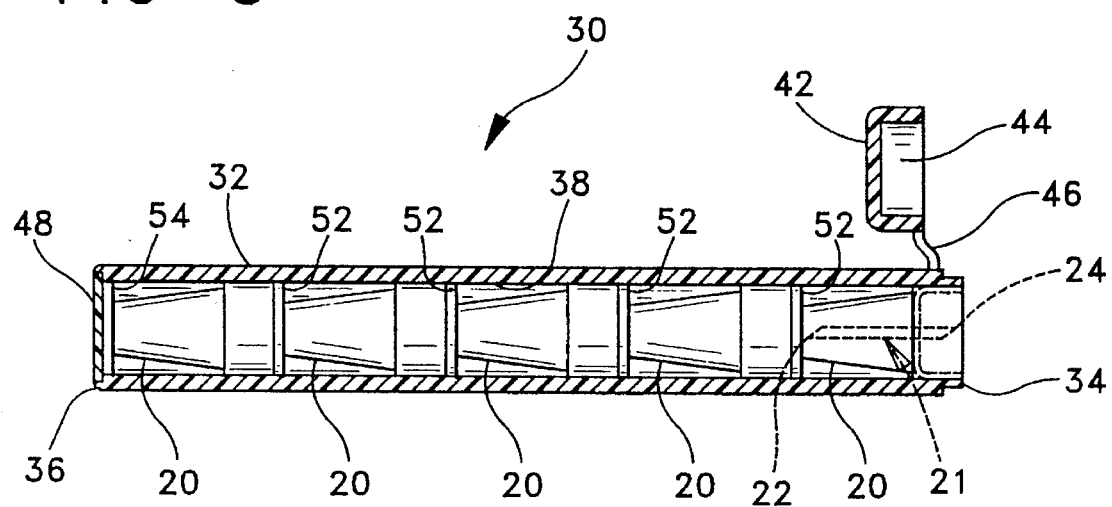
FIG. 5 is a cross-sectional view taken along line 5—5 in FIG. 4.
Figure 6:
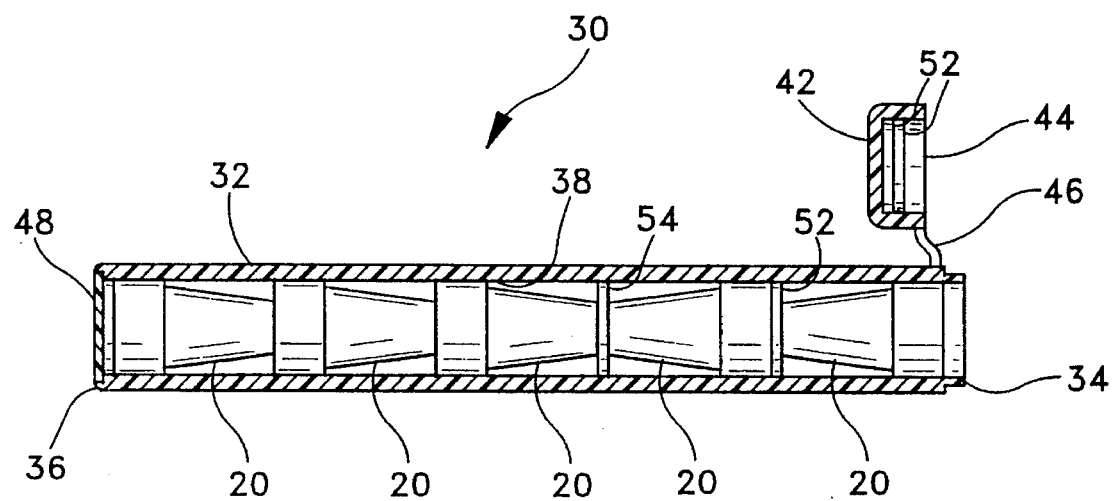
FIG. 6 is a cross-sectional view similar to FIG. 5, but showing the holder with three used needles.

It will be appreciated that apparatus 30 facilitates mounting of needle assemblies 20 to pen 10 and further facilitates removal and safe disposal of used needle assemblies 20. It will also be appreciated that separator disks 52 and end disk 54 will move incrementally toward dispensing end 34 each time a sterile needle assembly 20 is removed from apparatus 30 and a used needle assembly 20 is inserted into the opposed end of holder 32. This incremental movement of the disks can readily be observed through window 40. Thus, prior to the first use of apparatus 30, window 40 will display all color coded separator disks 52 as shown in FIGS. 2 and 5. After the first needle assembly has been removed, used and reinserted into inserting end 36, end disk 54 will become visible in the portion of window 40 nearer to inserting end 36. Color coded separator disks 52 will be visible through window 40 between sterile needle assemblies 20 that are disposed between end disks 54 and dispensing end 34 of holder 32. After the next needle assembly has been removed, used and inserted into holder 32, end disk 54 will move one increment closer to dispensing end 34. Additionally, there will be one less color coded separator disk 52 visible through window 40 and there will be two used needle assemblies 20 that are not separated by disks near the inserting end of holder 32. FIG. 6 shows holder 32 with two sterile needle assemblies 20 remaining.

The user of apparatus 30 will be warned when the last needle assembly in holder is available by the presence of only end disk 54 in window 40 and the presence of no color coded separator disks 52. No disks will be visible through window 40 when all needle assemblies have been used. At this point the user may safely discard the used and enclosed needle assemblies or may return the holder and used needle assemblies to a pharmacy or health care facility for proper disposal.

It should also be noted that after the last sterile needle assembly has been removed, used and inserted, holder 32 positively prevents a reuse of a used needle assembly. In this regard, used needle assemblies are inserted into holder 32 with their respective distal ends 22 pointing toward dispensing end 34 of holder 32. Needle assemblies 20 oriented in this manner can not be mounted to a medication delivery pen, in part due to interference between mating threads caused by fingers 50 of finger protection ring 48.

What is claimed is:

1. An apparatus for storing a plurality of needle assemblies and for selectively dispensing said needle assemblies therefrom, said apparatus comprising:

a plurality of sterile needle assemblies;

an elongate tubular holder having a passageway extending therethrough and being dimensioned for holding said plurality of said sterile needle assemblies in substantially end-to-end alignment, said holder having a dispensing end for selectively accessing said sterile needle assemblies for use and an insertion end for selectively inserting used needle assemblies for storage;

a lid releasably engaged over said dispensing end of said holder and hingedly connected to said dispensing end of said holder; and a guard mounted to said insertion end of said holder for preventing inadvertent contact with one of said sterile needle assemblies therein.

2. The apparatus of claim 1, further comprising a clip for securely connecting said holder to a medication delivery pen.

3. The apparatus of claim 1, wherein said holder includes an elongate window therein for viewing said passageway.

4. The apparatus of claim 3, further comprising a plurality of color coded separator disks disposed intermediate each of said sterile needle assemblies.

5. The apparatus of claim 4, further comprising an end disk disposed intermediate said sterile needle assemblies and said insertion end of said holder.

6. An apparatus for storing sterile needle assemblies, for selectively dispensing said sterile needle assemblies therefrom and for restoring said needle assemblies after use, said apparatus comprising:

a plurality of sterile needle assemblies, each said sterile needle assembly having a needle cannula with opposed proximal and distal ends, a mounting cap surrounding said proximal end of said needle cannula and a safety shield mounted over said distal end of said needle cannula and releasably engaged with said mounting cap, said sterile needle assemblies being substantially axially aligned with one another and having said respective distal end of each said needle cannula pointing in a common direction;

a plurality of separation disks intermediate said sterile needle assemblies;

an elongate tubular holder having a dispensing end, an insertion end and a passageway extending therebetween, said needle assemblies and said separator disks being slidably disposed in said passageways an elongate window formed through said holder and enabling observation of a plurality of said needle assemblies and separator disks in said passageway, whereby said proximal end of said needle cannula of each said needle assembly can be mounted to a hypodermic syringe and removed from said holder for use, and whereby said distal end of said needle cannula of each said needle assembly can be inserted into said inserting end of said holder after use and separated from said hypodermic syringe for storage.

7. The apparatus of claim 6, wherein said plurality of separator disks define a color and further comprising an end disk disposed intermediate said insertion end and said sterile needle assemblies and substantially adjacent one of said sterile needle assemblies, said end disk defining a color different from said color of said separator disks.

8. The apparatus of claim 6, further comprising a finger protection ring securely mounted to said insertion end for impeding access by a finger and preventing accidental needle sticks.

9. The apparatus of claim 6, further comprising a lid selectively removable from said dispensing end.

10. The apparatus of claim 9, wherein said lid is dimensioned for selectively storing a plurality of said separator disks.

11. The apparatus of claim 6, further comprising a clip for releasably attaching said holder to a hypodermic syringe.

12. A medication delivery system comprising:

a medication delivery pen having opposed proximal and distal ends and a medication cartridge contained therebetween, said distal end of said medication delivery pen including mounting structure;

a plurality of sterile needle assemblies, each said needle assembly having a needle cannula with opposed proximal and distal tips, a mounting cap secured to said needle cannula intermediate said opposed proximal and distal tips and having mounting structure for selectively engaging said mounting structure of said medication delivery pen, a safety shield mounted over said distal tip of said needle cannula and releasably engageable with said mounting cap, said needle assemblies being disposed in end-to-end alignment with one another such that said proximal tips all point in substantially a common direction;

a plurality of separator disks disposed respectively intermediate said needle assemblies;

a substantially tubular holder having a dispensing end, an opposed insertion end and a passageway extending therebetween, said needle assemblies and said separator disks being slidably disposed in said passageway such that the proximal point of each said needle cannula points toward said dispensing end, said holder having an elongate window formed therethrough for permitting observation of said separator disks, said dispensing end of said holder being dimensioned to receive said distal end of said medication delivery pen for enabling engagement of said distal end of said medication delivery pen with said mounting cap of one said needle assembly to enable removal of said needle assembly from said holder, said inserting end of said holder being dimensioned to sequentially receive distal portions of each said needle assembly therein after use for safely storing said needle assemblies after use.

13. The medication delivery system of claim 12, further comprising a mating clip releasably engaged to said holder and releasably engaged to said medication delivery pen for maintaining said holder and said medication delivery pen in proximity to one another.

14. The medication delivery system of claim 12, wherein said holder further includes a lid releasably engageable with said dispensing end.

15. The medication delivery system of claim 14, wherein said lid is dimensioned to retain said separator disks therein.

16. The medication delivery system of claim 12, further comprising an end disk disposed intermediate said sterile needle assemblies and said insertion end of said holder, said end disk being incrementally movable toward said dispensing end of said holder as needle assemblies are used and inserted into said inserting end of said holder.

17. The medication delivery system of claim 16, wherein said separator disks are of a first color, and wherein said end disk is of a second color.

18. The medication delivery system of claim 12, wherein said holder further includes a finger protection ring fixedly mounted to said insertion end for preventing inadvertent contact with said needle assemblies therein.

19. A method for storing, using and dispensing pen needles with a medication delivery pen, each said pen needle having an elongate needle cannula with opposed proximal and distal tips and a mounting cap securely mounted to said needle cannula intermediate said tips and substantially surrounding said proximal tip, said method comprising the steps of:

providing an elongate substantially tubular holder having a dispensing end, an insertion end and a substantially tubular passageway extending therebetween;

inserting a plurality of said pen needles in said holder in substantially end-to-end relationship with one another, such that said proximal point of each said needle cannula points toward said dispensing end of said holder, and such that one said pen needle is substantially adjacent said dispensing end;

mounting said medication delivery pen to said pen needle adjacent said dispensing end of said holder;

removing said pen needle mounted to pen from said holder;

using said pen;

inserting said used pen needle into said inserting end of said holder and thereby urging remaining ones of said pen needles toward said dispensing end of said holder; and separating said medication delivery pen from said pen needle and said holder.

20. The method of claim 19, wherein each said pen needle further includes a safety shield protectively enclosing said distal tip of said needle cannula and releasably engaged with said mounting cap, and wherein said method further includes the steps of separating said safety shield from said needle cannula and said mounting cap prior to use of said medication delivery pen, and replacing said safety shield over said distal tip of said needle cannula and onto said mounting cap prior to inserting said pen needle into said inserting end of said holder.

* * * * *